(12) United States Patent
Ferris et al.

(10) Patent No.: US 9,295,793 B2
(45) Date of Patent: Mar. 29, 2016

(54) INHALER DEVICE AND METHOD OF ADMINISTERING A MEDICAMENT

(75) Inventors: Christopher Ferris, Arlesey (GB); Matthew Young, Over (GB); Jonathan Oakley, Eynesbury (GB); Wayne O'Hara, Dunedin (NZ)

(73) Assignee: AVENTIS PHARMA LIMITED, West Malling, Kent (GB)

( * ) Notice: Subject to any disclaimer, the term of this patent is extended or adjusted under 35 U.S.C. 154(b) by 1554 days.

(21) Appl. No.: 11/910,678

(22) PCT Filed: Apr. 7, 2006

(86) PCT No.: PCT/GB2006/050081
§ 371 (c)(1),
(2), (4) Date: Jun. 3, 2008

(87) PCT Pub. No.: WO2006/106367
PCT Pub. Date: Oct. 12, 2006

(65) Prior Publication Data
US 2009/0114219 A1    May 7, 2009

(30) Foreign Application Priority Data
Apr. 8, 2005 (GB) .................................. 0507100.6

(51) Int. Cl.
*A61M 15/00* (2006.01)
*A61M 16/00* (2006.01)

(52) U.S. Cl.
CPC ....... *A61M 15/0065* (2013.01); *A61M 15/0081* (2014.02); *A61M 15/0095* (2014.02); *A61M 2016/0021* (2013.01); *A61M 2202/066* (2013.01)

(58) Field of Classification Search
CPC ..................... A61M 15/0065; A61M 15/0081; A61M 15/0095; A61M 16/0021; A61M 2202/066; A61M 15/0001; A61M 15/002; A61M 15/0068; A61M 15/007; A61M 15/0071; A61M 15/0091; A61M 2016/0021

USPC ........... 128/203, 14, 203.15, 203.19, 200.19, 128/200.22, 200.23, 203.12, 203.21, 128/203.23–203.24, 204.18, 128/204.24–204.25, 205.23–205.24

See application file for complete search history.

(56) References Cited

U.S. PATENT DOCUMENTS 3,636,949 A * 1/1972 Kropp ...................... 128/200.23
4,106,503 A   8/1978 Rosenthal et al.

(Continued)

FOREIGN PATENT DOCUMENTS

| WO | WO 92/07599 | 5/1992 |
| WO | WO 97/00703 | 1/1997 |
| WO | WO 2004/028608 | 4/2004 |

*Primary Examiner* — Tan-Uyen (Jackie) T Ho
*Assistant Examiner* — Mark K Han
(74) *Attorney, Agent, or Firm* — Scully, Scott, Murphy & Presser, P.C.; Bernhard Schupp (57) ABSTRACT

An inhaler device (1) contains, or is capable of accepting, a plurality of doses of a medicament to be dispensed from the inhaler (1). To ameliorate the problem of double dosing from the inhaler (1), the device further comprises prevention means (26, 28, 40) for preventing, at least temporarily, the dispensing of a dose of medicament, and detection means (32) for detecting the inhalation of a previously dispensed dose of medicament. When the detection means (32) detects the inhalation of the previously dispensed dose of medicament, it releases the prevention means (26, 28, 40), allowing the device to dispense a further dose of medicament. The detection means (32) may be a pressure sensor, and the prevention means (26, 28, 40) may operate by causing a disengagement of an actuation mechanism.

23 Claims, 6 Drawing Sheets

(56) References Cited

U.S. PATENT DOCUMENTS

| | | | | |
|---|---|---|---|---|
| 4,664,107 | A * | 5/1987 | Wass | 128/200.23 |
| 4,934,358 | A | 6/1990 | Nilsson et al. | |
| 5,119,806 | A * | 6/1992 | Palson et al. | 128/200.14 |
| 5,284,133 | A | 2/1994 | Burns et al. | |
| 5,363,842 | A | 11/1994 | Mishelevich et al. | |
| 5,447,151 | A | 9/1995 | Bruna et al. | |
| 5,487,378 | A | 1/1996 | Robertson et al. | |
| 5,497,764 | A * | 3/1996 | Ritson | A61M 15/00 128/200.14 |
| 5,505,195 | A * | 4/1996 | Wolf et al. | 128/203.15 |
| 5,507,277 | A | 4/1996 | Rubsamen et al. | |
| 5,655,516 | A | 8/1997 | Goodman et al. | |
| 5,678,538 | A * | 10/1997 | Drought | 128/203.15 |
| 5,692,492 | A * | 12/1997 | Bruna et al. | 128/200.23 |
| 5,694,919 | A | 12/1997 | Rubsamen et al. | |
| 5,735,263 | A | 4/1998 | Rubsamen et al. | |
| 5,755,218 | A * | 5/1998 | Johansson et al. | 128/200.14 |
| 5,794,612 | A | 8/1998 | Wachter et al. | |
| 5,813,397 | A | 9/1998 | Goodman et al. | |
| 5,826,570 | A | 10/1998 | Goodman et al. | |
| 5,971,951 | A * | 10/1999 | Ruskewicz | 604/62 |
| 6,012,454 | A * | 1/2000 | Hodson et al. | 128/203.15 |
| 6,089,227 | A | 7/2000 | Nilsson | |
| 6,167,880 | B1 | 1/2001 | Gonda et al. | |
| 6,182,655 | B1 * | 2/2001 | Keller et al. | 128/203.15 |
| 6,260,549 | B1 * | 7/2001 | Sosiak | 128/200.23 |
| 6,325,062 | B1 | 12/2001 | Sosiak | |
| 6,357,442 | B1 * | 3/2002 | Casper et al. | 128/200.23 |
| 6,390,088 | B1 | 5/2002 | Nohl et al. | |
| 6,425,392 | B1 | 7/2002 | Sosiak | |
| 6,435,175 | B1 | 8/2002 | Stenzler | |
| 6,557,550 | B1 * | 5/2003 | Clarke | A61M 15/0065 128/203.15 |
| 6,615,825 | B2 | 9/2003 | Stenzler | |
| 6,718,972 | B2 * | 4/2004 | O'Leary | 128/203.15 |
| 6,729,330 | B2 | 5/2004 | Scarrott et al. | |
| 6,752,147 | B1 | 6/2004 | Goldemann et al. | |
| 6,823,863 | B2 * | 11/2004 | Huxham et al. | 128/200.23 |
| 6,948,492 | B2 | 9/2005 | Wermelling et al. | |
| 6,948,495 | B2 | 9/2005 | Seppala | |
| 6,971,381 | B2 | 12/2005 | Langford | |
| 6,990,975 | B1 | 1/2006 | Jones et al. | |
| 7,004,164 | B2 | 2/2006 | Scarrott | |
| 7,047,964 | B2 * | 5/2006 | Bacon | 128/200.23 |
| 7,905,230 | B2 * | 3/2011 | Schuler et al. | 128/200.23 |
| 8,651,103 | B2 * | 2/2014 | Barney et al. | 128/203.15 |
| 2002/0000225 | A1 | 1/2002 | Schuler et al. | |
| 2002/0157662 | A1 | 10/2002 | Stenzler | |
| 2002/0195101 | A1 | 12/2002 | Scheuch | |
| 2003/0101991 | A1 | 6/2003 | Trueba | |
| 2003/0205229 | A1 | 11/2003 | Crockford et al. | |
| 2004/0065321 | A1 | 4/2004 | Stenzler | |
| 2004/0107961 | A1 | 6/2004 | Trueba | |
| 2004/0231669 | A1 | 11/2004 | Bruna | |
| 2005/0011515 | A1 * | 1/2005 | Lee et al. | 128/200.23 |
| 2005/0022806 | A1 * | 2/2005 | Beaumont | A61M 15/0065 128/200.14 |
| 2006/0021614 | A1 | 2/2006 | Wermeling et al. | |
| 2006/0037612 | A1 | 2/2006 | Herder et al. | |
| 2006/0124129 | A1 * | 6/2006 | Wharton et al. | 128/204.26 |

\* cited by examiner

INHALER DEVICE AND METHOD OF ADMINISTERING A MEDICAMENT

This invention relates to an improved inhaler device and to a method of administering a medicament by means of an inhaler.

Inhaler devices for administering medicaments are well known, eg inhalers for asthma sufferers. In particular, it is known to provide an inhaler device which contains a plurality of doses of a medicament, so that the inhaler can be re-used before requiring replenishment with medicament.

A problem with such multi-dose inhalers is that they may allow for the deliberate or inadvertent dispensing of two or more doses of medicament ("repeat dosing" or "double dosing"). Inadvertent double dosing may occur, for instance, when a user dispenses a dose of medicament, but is not sure that he has done so and so dispenses another dose. This may happen because dosing is not accompanied by any audible or other indication that confirms that a dose has effectively been dispensed. Another situation in which double dosing may occur is when a user dispenses a dose, but is then distracted prior to inhaling the dose. The user may then forget that a dose has already been dispensed, and therefore dispenses another dose.

For metered dose inhalers (MDIs), that use pressurised drug formulations containing volatile propellants, the problem of double dosing is relatively slight, as a dose is dispersed as soon as it is dispensed. For many types of dry powder inhalers (DPIs), however, the problem of double dosing is particularly acute as the dispensing of the dose and the entrainment of the dispensed powder in an inhaled airflow are often entirely separate actions. It is therefore possible for more than one dose of medicament to accumulate within the device and for that excessive dose then to be inhaled.

This problem has been addressed in a number of ways. One solution proposed has been the provision of a visible indication that a dose has already been dispensed. However, this relies on the user noticing the visible indication.

It is an object of the present invention to provide a multi-dose inhaler device which ameliorates the problem of inadvertent repeat-dosing. In particular, the invention aims to provide a multi-dose inhaler device which will not dispense a second dose of a medicament, at least temporarily, until a previously-dispensed dose has been inhaled.

In a first aspect the invention provides an inhaler device having, or capable of accepting, a plurality of doses of a medicament to be dispensed by the inhaler, the device further comprising: prevention means for preventing, at least temporarily, the dispensing of a dose of medicament; and detection means for detecting the inhalation of a previously dispensed dose of medicament; whereby when the detection means detects the inhalation of the previously dispensed dose of medicament, it releases the prevention means, allowing the device to dispense a further dose of medicament.

The inhaler device according to the invention is advantageous primarily in that the prevention means prevents, at least temporarily, the dispensing of a dose of medicament until an indication has been received that a previously dispensed dose has been inhaled.

Typically the inhaler device comprises an actuation or priming mechanism, which must be operated by the user in order to enable the device to dispense a dose of medicament. Conveniently the actuation mechanism comprises a manually operable actuation means, such as a switch, trigger, twist-action element or the like.

In a preferred embodiment, the prevention means acts on, and/or is associated with, the actuation mechanism. For example, in one embodiment, an initial operation of the actuation mechanism primes the inhaler so as to dispense, or enable dispensing, of a dose of medicament, but a further movement or operation of the actuation mechanism operates the prevention means, thereby preventing, at least temporarily, the dispensing of a further dose.

The "initial operation" and "further movement" of the actuation mechanism may represent different extents of movement in the same sense. For example, an initial twist action may cause or enable dispensing of a dose of medicament, and further twisting in the same sense may operate the prevention means. Alternatively, the "further movement" may be a reciprocal movement (ie a movement in the opposite sense or direction to that ("the initial operation") which causes or enables the dispensing of a dose of medicament). For example, where the actuation mechanism comprises a switch, an initial movement (eg depression) of the switch in a first direction may prime the inhaler and dispense a dose of medicament, but a second, reverse, movement operates the prevention means. Desirably, biasing means, such as a spring, may be employed to cause a reverse movement of the actuation mechanism when it is released by the user after the initial movement has been effected.

It is preferred that the prevention means operates by causing a disengagement of the actuation mechanism (eg a functional, typically physical, separation of two components which are required to interact in order for the inhaler to be actuated). Such disengagement is preferred to the deployment of a barrier or obstacle to seize the mechanism, since the latter arrangement might encourage the user to try to overcome the resistance provided by the barrier or obstacle, and this might lead to damage to the actuation mechanism and/or the prevention means. Nevertheless, deployment of a barrier or obstacle to seize up the actuation mechanism constitutes one possible embodiment, albeit not preferred, of the present invention.

In preferred embodiments of the invention, disengagement of components that form part of the actuation mechanism is brought about by a camming action, in which the components undergo relative movement and a cam follower on one of the components is caused to move from a first position, in which the components are engaged, to a second position, in which the components are disengaged. The relative movement of the two components is preferably brought about manually by the user of the inhaler, eg by a sliding or rotational movement of one of the components.

Preferably the detection means comprises a pressure sensor, more preferably a micro electromechanical systems (MEMS) pressure sensor. A number of MEMS pressure sensors are commercially available and suitable for use in the present invention, including those obtainable from Freescale Semiconductor Inc. (USA).

A pressure sensor has been found to be most suitable, since (i) it is directly responsive to inhalation by a user, and (ii) it does not obstruct or otherwise interfere with the flow of air or medicament through or from the inhaler.

The pressure sensor is capable of detecting the reduction in pressure which takes place when a user inhales air from the inhaler device. Conveniently the detection means is arranged such that it releases (or permits the release of) the prevention means (thereby allowing, for example, re-engagement of the actuation mechanism) in response to a certain magnitude of pressure reduction. Typically the magnitude of pressure change to which the device responds is a reduction of about 40-60 mbar, preferably about 50 mbar, which is a magnitude of pressure change which is usually attained or exceeded by a subject when inhaling a medicament.

More preferably, however, the detection means is responsive not only to the magnitude of the pressure change. It has been found that pressure reductions of the order of 50 mbar or so can be caused by events other than user inhalation (eg by sudden draughts due to, for instance, slamming doors or the like). Accordingly, in a preferred embodiment, the detection means is also sensitive to the duration of the pressure change, since inhalatory events normally last at least one second, whereas pressure changes due to other causes are usually of very brief duration.

Desirably, the detection means is responsive only to a pressure reduction of a predetermined magnitude which persists for a predetermined length of time. For instance, the pressure reduction may have a magnitude of about 40-60 mbar, preferably about 50 mbar, and may last for at least one second, eg 1-3 seconds or 1.5-2.5 seconds, preferably about 2 seconds.

The detection means is most preferably positioned in, or in the vicinity of, the outlet or mouthpiece via which the dose of medicament is inhaled by the user, as it is at this location that the drop in pressure that occurs upon inhalation is greatest.

Preferably the inhaler device of the present invention comprises one or more signal processing means. In particular, the device conveniently comprises: a microprocessor, especially a microprocessor chip, for processing signals; an amplifier for amplifying a signal output from the pressure sensor; and signal filter means eg a low-pass filter. Conveniently these elements are arranged, together with the detection means and/or the prevention means, in a microelectromechanical circuit.

In certain embodiments, after a dose of medicament has been dispensed, the actuation mechanism is held in a disengaged state by the action of the prevention means. The actuation mechanism may be held in the disengaged state by electromechanical means, eg by a motor or solenoid. When inhalation is detected by the detection means, the current to the motor or solenoid may be cut or reduced, allowing the actuation mechanism to re-engage. More preferably, however, the actuation mechanism is held in the disengaged state by a purely mechanical means that does not rely on a supply of electrical power. Most preferably, such mechanical means includes a latch mechanism that engages when components of the actuation mechanism are disengaged and then maintains the components in the disengaged state until the latch is released. Most preferably, a component of the actuation mechanism is formed with resilient detents that are adapted to hold that component in a position spaced apart from another component with which the first component is normally engaged, and which can be released to permit re-engagement of the two components. Most preferably, release of the detents is brought about by electromechanical means. Such embodiments are preferred because power is required to be supplied only momentarily, to permit release of the latch mechanism, rather than continuously for the whole of the period for which the actuation mechanism is in the disengaged state.

In addition to the detection means that is able to detect inhalation of a dose of medicament, the inhaler device may comprise one or more further sensors, and release of the prevention means may be dependent on signals received from those sensors, as well as, or instead of, the signal received from the detection means.

The inhaler device according to the invention may be any one of numerous different forms of such device. Most preferably, however, the inhaler device is a dry powder device, in which the dose of medicament takes the form of a unit dose of powdered medicament formulation. The device may be a multi-dose device in which unit doses of medicament are metered from a bulk reservoir of medicament formulation, or it may be a device containing a plurality of unit doses that are individually dispensed, eg by being held in separate compartments in a cartridge that is indexed through some form of opening station within the device.

In a second aspect the invention provides a method of administering a dose of a medicament to a subject, the method comprising the use of an inhaler device in accordance with the first aspect of the invention.

Embodiments of the invention will now be described in greater detail, by way of illustration only, with reference to the accompanying drawings.

Figure 1:
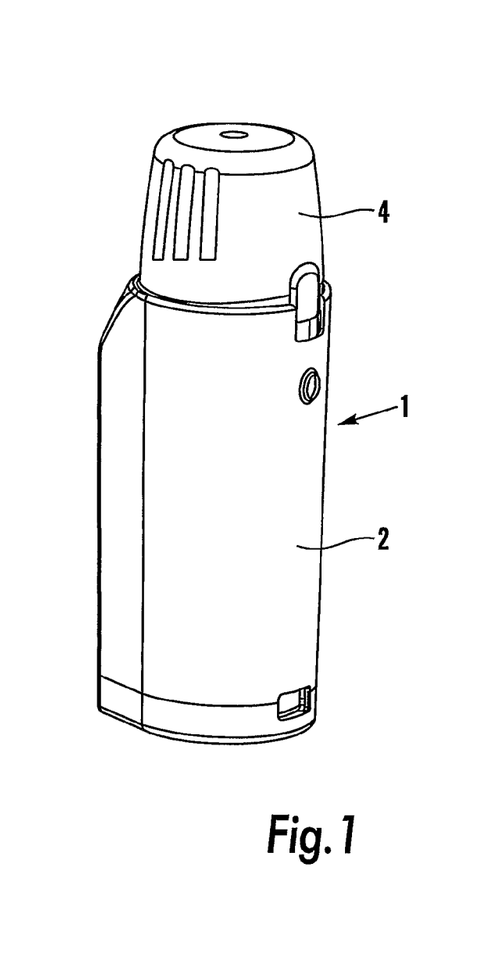
FIG. 1 is a perspective view of a dry powder inhaler in accordance the invention.
Figure 2:
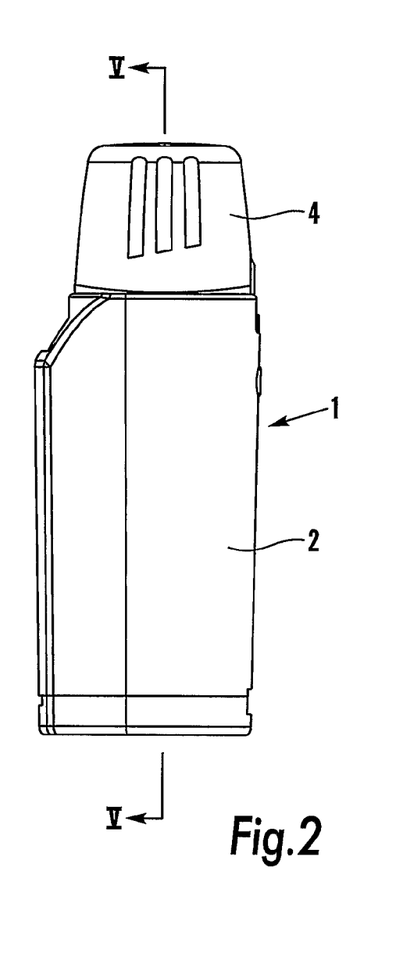
FIG. 2 is a side elevation of the inhaler of FIG. 1.
Figure 3:
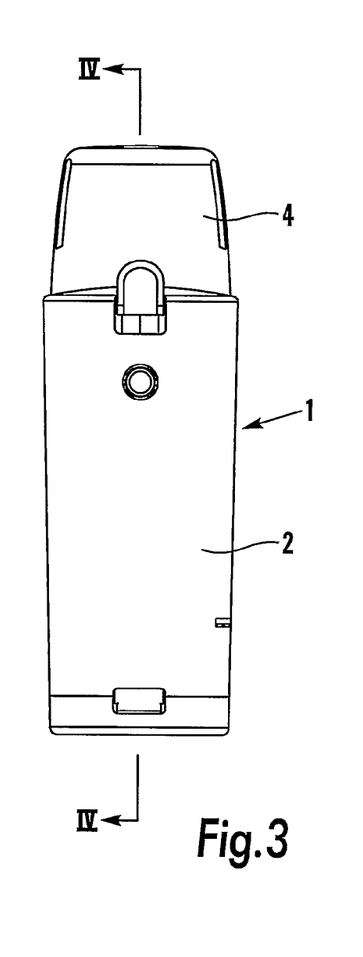
FIG. 3 is a front elevation of the inhaler of FIG. 1.

Referring first to FIGS. 1 to 3, a dry powder inhaler in accordance with the invention is generally designated 1. The inhaler 1 is dimensioned such that it can easily be held and manipulated in a user's hands. The inhaler comprises a body, the outer surface of which is defined by a sleeve 2 that surrounds a medicament reservoir and dose dispensing mechanism (described in more detail below). A mouthpiece 3 (not visible in FIGS. 1 to 3) extends from the upper (as viewed in the Figures) end of the body and is covered by a removable cap 4.

The nature of the dose dispensing mechanism is not critical to the present invention, but in the illustrated embodiment is a mechanism that is generally as described in EP-A-0407028, EP-A-0691865 and WO-A-99/21601. The construction and mode of operation of the dose dispensing mechanism may be described as follows.

Figure 4:
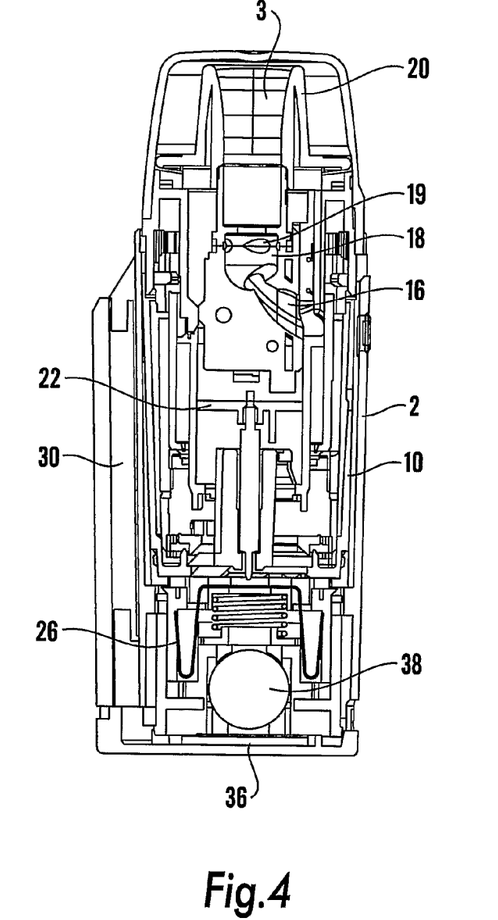
FIG. 4 is a cross-sectional view along the line IV-IV in FIG. 3.
Figure 5:
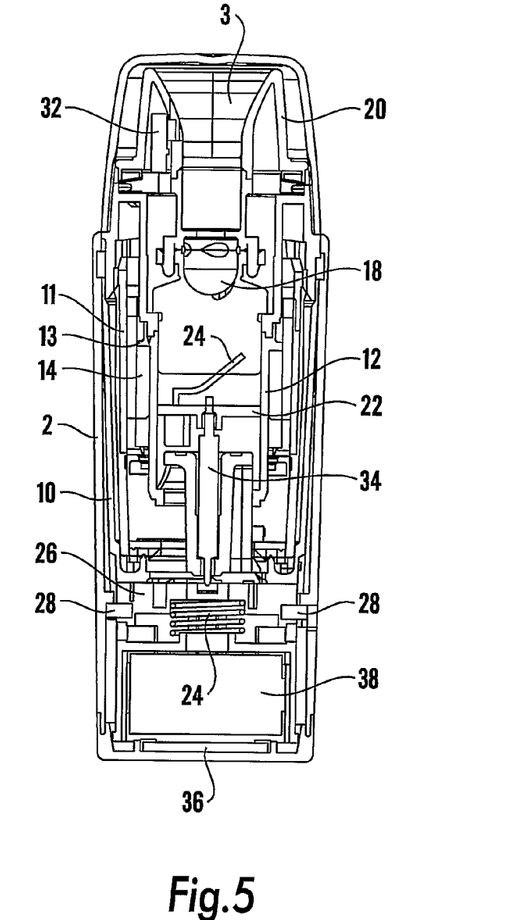
FIG. 5 is a cross-sectional view along the line V-V in FIG. 2.

Referring now to FIGS. 4 and 5, a generally cylindrical barrel 10 is housed within the sleeve 2. A generally cylindrical container 11 fits closely within the barrel 10, and defines, together with a cylindrical mandrel 12 that is of lesser diameter than the container 11 and is mounted coaxially with the container 11, an annular medicament reservoir 14. The reservoir 14 is charged with a compacted body of powdered inhalation medicament.

The barrel 10 (and hence the container 11 and compacted body of medicament contained within the reservoir 14) is adapted for limited rotation through a predetermined angle, which is typically 60°. The manner by which rotation of the barrel 10 is brought about is described below.

The upper (as viewed in the drawings) end of the mandrel 12 is formed with a helical blade 13. Rotation of the compacted body of medicament causes the blade 13 to cut or abrade a dose of medicament from the bulk quantity contained in the reservoir 14. That dose of medicament passes via a duct 16 to a dispersion chamber 18 that has tangential air inlets 19 and which is in communication with the mouthpiece 20.

In order to improve dose dispensing accuracy, and to prevent medicament being dispensed from the reservoir 14 into the duct 16 and dispersion chamber 18 inadvertently, for instance if the inhaler 1 is subjected to mechanical shock, as when dropped, the inhaler 1 includes a shuttering mechanism similar to that described in EP-A-0691865. The shuttering mechanism comprises a metal blade that is mounted on a carrier 22 which is adapted to move axially between a first/rest position and a second/metering position. In the first/rest position the compacted body of medicament contained with the reservoir 14 is isolated from the duct 16. In the second/metering position the compacted body of medicament is exposed to the duct 16. The end of the carrier 22 that is remote from the shutter blade has a formation that bears on a cam surface formed on the internal surface of the barrel 10. The carrier 22 is biased against the cam surface by a half cantilever 24 provided on the carrier 22. The effect of the cam surface is to displace the carrier 22 axially, from the first/rest position to the second/metering position, when the barrel 10 is rotated, so that a dose of medicament cut from the compacted body of medicament within the reservoir 14 can pass into the duct 16 and dispersion chamber 18. After dispensing of the dose, when the barrel 10 is rotated in the reverse direction, the carrier 22 returns to the first/rest position in which the medicament is isolated from the duct 16.

To the extent described above, the inhaler 1 is generally similar to that disclosed in EP-A-0691865. The inhaler 1 differs from that earlier disclosure in the following respects.

First, the barrel 10 (and hence the compacted body of medicament in the reservoir 14) is urged into contact with the helical blade 13 by a compression spring 24 that acts, not directly on the closed, lower end of the barrel 10, but on a shuttle 26 that is interposed between the spring 24 and the barrel 10. The shuttle 26 is urged by the spring 24 into abutment and engagement with the lower end of the barrel 10 such that rotation of the shuttle 26 causes rotation of the barrel 10. The shuttle 26 is, however, not fixedly attached to the barrel 10 and is capable of axial displacement from the barrel 10, against the action of the spring 24.

A pair of drive pins 28 project outwardly from the shuttle 26 and engage in grooved tracks formed in the internal surface of the sleeve 2. The interaction of the drive pins 28 and the grooved tracks is described below with reference to FIG. 6.

The inhaler 1 is provided with electronic means intended to eliminate or reduce the possibility of undesired double dosing of medicament. These means comprise three principal components, viz a printed circuit board (PCB) 30 that is housed within the sleeve 2, a MEMS pressure sensor 32 located within the mouthpiece 3, and a carrier position sensor 34 that is adapted to sense the position of the shutter carrier 22. The carrier position sensor 34 takes the form of a single pole switch. A battery 36 to provide power to the PCB 30 is housed in the lower end portion of the inhaler 1, as is a second battery 38 that provides power to a shuttle release mechanism that is described more fully below.

In use, when it is desired to dispense a dose of medicament from the reservoir 14, the sleeve 2 is rotated by the user in the direction of the arrow A in FIG. 1. The drive pins 28 are engaged in grooved tracks 40 formed on the internal surface of the sleeve 2. These tracks 40, and the manner in which they interact with the drive pins 28, are illustrated in FIG. 6, in which the direction of movement of the sleeve 2 is indicated by the arrows.

Figure 6:
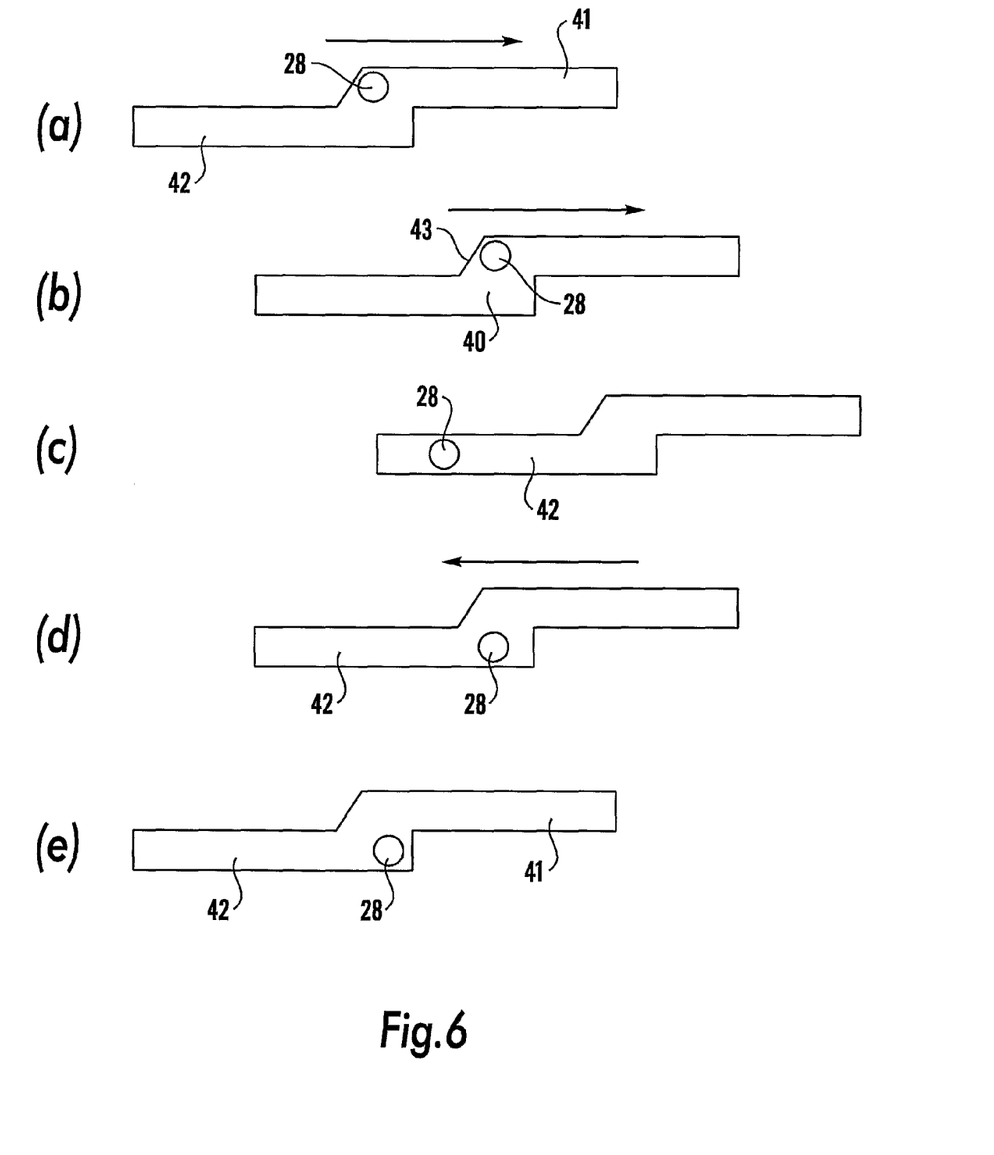
FIG. 6 illustrates schematically the interaction of a sleeve and drive shuttle forming part of the inhaler of FIG. 1, during actuation of the inhaler to dispense a dose of medicament from a medicament reservoir.

Each grooved track 40 is cranked, and comprises an upper limb 41 and a lower limb 42 that are parallel but extend in opposite directions from the initial position of the drive pin 28 (FIG. 6a). In the region where the upper limb 41 and lower limb 42 overlap, the end of the upper limb 41 is formed as a ramp 43.

Initially, the drive pin 28 resides at the position shown in FIG. 6a, in the upper limb 41 of the track 40, and adjacent to the ramp 43. Rotation of the sleeve 2, in the direction indicated by the arrow in FIG. 6a, causes the ramp 43 to bear on the drive pin 28, thereby urging the drive pin 28 in the same direction and causing the shuttle 26, and hence the barrel 10, to rotate. Rotation of the barrel 10 also causes the shutter carrier 22 to move from the first/rest position to the second/metering position.

Rotational displacement of the drive pin 28 continues until the barrel 10 reaches the end of its rotational travel (FIG. 6b).

Further rotation of the sleeve 2 then causes the drive pin 28 to be displaced relative to the track 40. In particular, the drive pin 28 travels down the ramp 43 and along the lower limb 42 of the track 40 (FIG. 6c).

Figure 7:
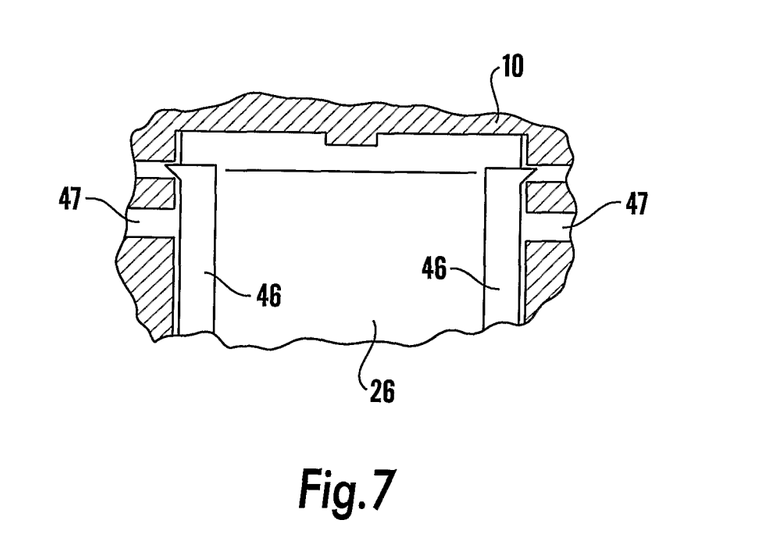
FIG. 7 is a fragmentary cross-sectional view showing the drive shuttle in a first, engaged position.
Figure 8:
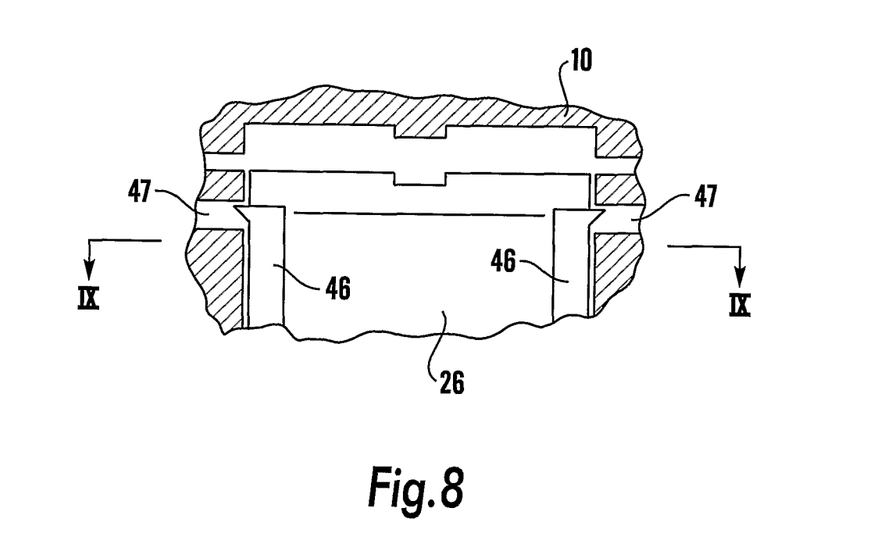
FIG. 8 is a view similar to FIG. 7, but showing the drive shuttle in a second, disengaged position.

The effect of the displacement of the drive pin 28 from the upper limb 41 to the lower limb 42 of the track 40 is to displace the shuttle 26 from the lower end of the barrel 10, against the action of the spring 24. The shuttle 26 and the barrel 10 are thus disconnected. Moreover, the shuttle 26 is retained in the disconnected condition by a pair of latches 46 that are deformed inwardly during the downwards axial movement of the shuttle 26 and engage in slots 47 formed in the wall of the component within which the shuttle 26 travels. This is illustrated in more detail in FIGS. 7 and 8 (in which much detail is omitted for clarity).

Once the drive pin 28 has reached the full extent of its travel within the lower limb 42 of the track 40, and the shuttle 26 has latched in the disconnected condition, further rotation of the sleeve 2 is not possible. Rotation of the sleeve 2 in the reverse direction then causes relative movement of the drive pin 28 along the lower limb 42 to the area of overlap of the upper and lower limbs 41,42 (FIG. 6d). The inward end of the lower limb 42 is, however, not formed as a ramp, and so continued reverse rotation draws the drive pin 28 back to a position (FIG. 6e) in which its radial position is that at which it started (ie as in FIG. 6a), but at which it is displaced axially from its starting position. Reverse rotation of the sleeve 2 also returns the shutter carrier 22 to the first/rest position, which is detected by the carrier position sensor 34.

So long as the shuttle 26 remains in the latched, disengaged position, rotation of the sleeve 2 has no effect on the barrel 10 and hence cannot lead to dispensing of another dose from the medicament reservoir 14. The PCB 30 carries a processor that is programmed to release the shuttle 26 from its latched, disengaged position only if two conditions are satisfied after a dose has been dispensed. These conditions are:
1) that inhalation of the dispensed dose has been detected by the pressure sensor 32 located within the mouthpiece 3; and
2) that the shutter carrier 22 has returned to its first/rest position, as detected by the carrier position sensor 34.

Figure 9:
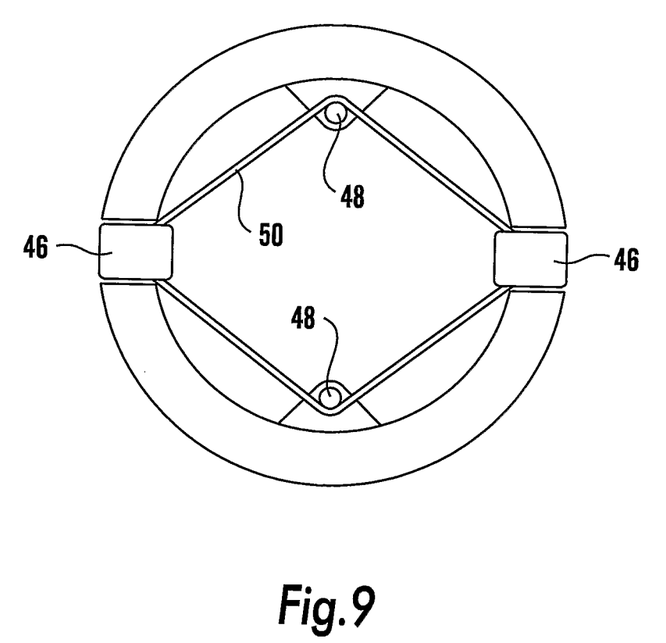
FIG. 9 is a cross-sectional view on the line IX-IX of FIG. 8.

Once both of these conditions are satisfied, the shuttle 26 is released. The mechanism by which this is achieved is illustrated in FIG. 9. A loop of wire 50 of a shape memory alloy (specifically the nickel/titanium alloy known as Nitinol) is passed around or through the latches 46 and a pair of upstands 48 formed integrally with the shuttle 26. At room temperature, the wire 50 is in a so-called martensitic phase, but application of an electric current causes the metal to pass through a transition temperature and to undergo a phase change to the austenitic phase. This phase change is accompanied by a reduction in length of the wire loop 50, which causes the loop 50 to contract and hence to pull the latches 46 out of engagement with the slots 47. Thus, after a dose of medicament has been dispensed from the reservoir 14, the PCB 30 awaits a signal from the pressure sensor 32 to confirm that inhalation has occurred and a signal from the carrier position sensor 34 to confirm that the shuttle carrier 22 has returned to its first/rest position. If both signals are received, then the PCB 30 causes current to be supplied to the wire loop 50. The wire loop 50 contracts, drawing the latches 46 inwards (as indicated by the arrows in FIG. 9), releasing the latches 46 from the slots 47. The shuttle 26 is then displaced, under the action of the spring 24, back into engagement with the barrel 10. The shuttle 26 and drive pins 28 have then returned to their original positions (ie as shown in FIGS. 4, 5, 6 and 7).

In this manner, the dispensing of a second dose of medicament from the reservoir 14 is prevented until indications have been received by the PCB 30 to the effect that the previously dispensed dose has been inhaled. The shuttle 26 may, however, also be released after a predetermined time period, eg 10 minutes, even if no inhalation is detected.

Figure 10:
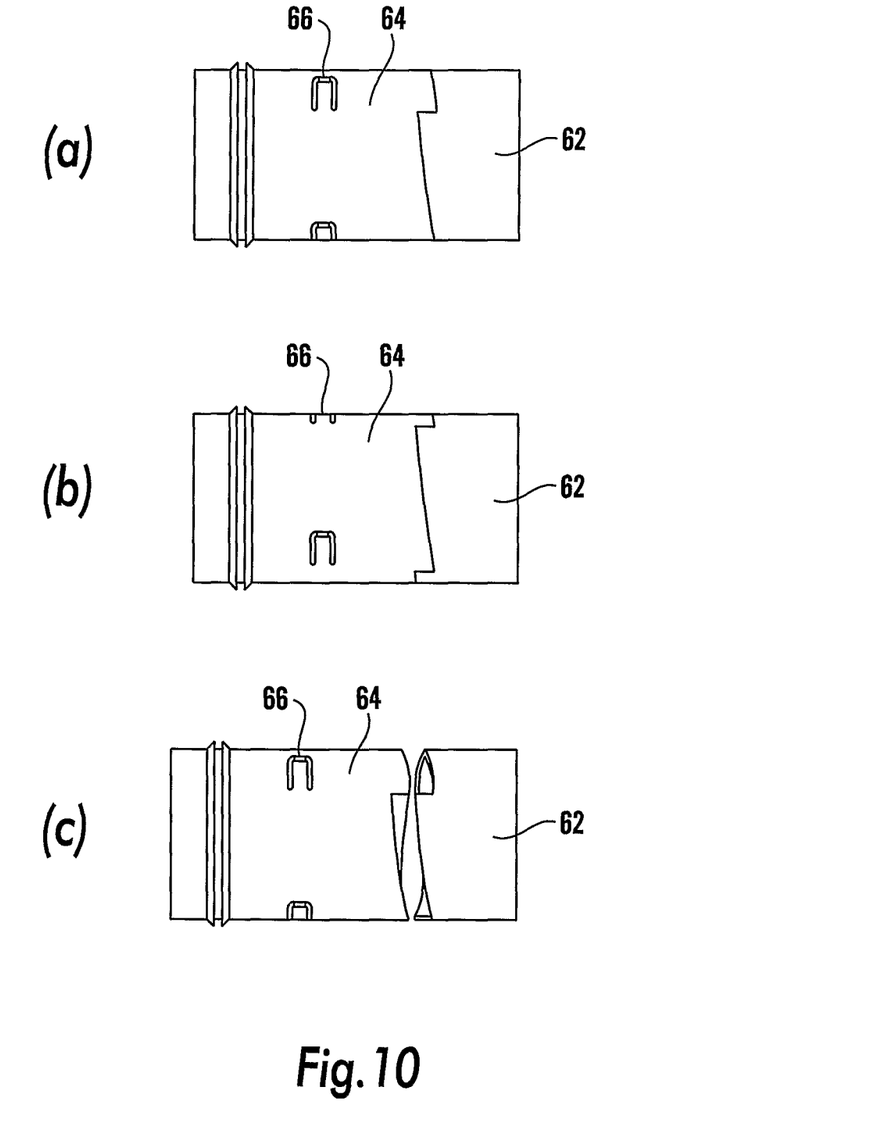
FIG. 10 illustrates schematically an alternative embodiment of an actuation mechanism forming part of an inhaler according to the invention.

Finally, FIG. 10 illustrates schematically an alternative embodiment of an actuation mechanism forming part of an inhaler according to the invention.

In this embodiment, the actuation mechanism comprises an actuation cap 62 and an actuation collar 64, both of which rotate within a generally cylindrical housing (not shown). The cap 62 and collar 64 are initially in an engaged state (FIG. 10*a*), in which stepped profiles of the respective surfaces of the cap and collar are interlocked. To prime the device, in order to dispense a dose of medicament, the user twists the cap 62 in a clockwise direction (which appears in the side view shown in FIG. 10 as a rotation from the bottom towards the top). This causes corresponding rotation of the collar 64 because of the interlocking surfaces of the collar 64 and cap 62.

After a desired degree of rotation of the collar 64 has been achieved (FIG. 10*b*), one or more projections 66 on the collar become engaged with one or more corresponding respective recesses on the inner surface of the housing (not shown), causing the collar 64 to be locked in position.

Twisting of the cap 62, however, is performed against the action of a biasing means, such as a spring (not shown), such that when the user releases the cap 62, it returns to its start position. The respective surfaces of the cap 62 and collar 64 are so profiled that the return movement of the cap 62 forces the collar 64 away from the cap 62, so that the two components become disengaged (FIG. 10*c*). Preferably, the movement of the collar 64 away from the cap 62 is also against the action of a biasing means, such as a spring.

The cap 62 and collar 64 are then held in this disengaged state, typically by an electromechanical system (such as a solenoid or motor), until inhalation by the user is detected or until the system is reset. In practice, in order to conserve power, the device will typically reset after a period of time (eg 10 minutes) if no inhalation has been detected in the interim. When inhalation is detected, or the system is reset, the collar 64 is released (eg by cutting the power to the motor or solenoid) allowing the collar 64 to move back into engagement with the cap 62, ready for dispensing of a further dose of medicament.

It will be appreciated that many of the features described with specific reference to the embodiments described in detail above may be utilised in a wide variety of different inhaler devices, and those features are not necessarily always used in combination with each other.

The invention claimed is:

1. An inhaler device having, or capable of accepting, a plurality of doses of a medicament to be dispensed by the inhaler device, the inhaler device further comprising:
   an actuation mechanism, said actuation mechanism including components comprising an interlocking collar, a cap, a housing and biasing means, which must be operated by a user in order to enable the inhaler device to dispense a dose of medicament;
   prevention means for preventing, at least temporarily, the dispensing of the dose of medicament by causing a disengagement of two components of the actuation mechanism brought about by a camming action, in which the two components undergo relative movement and a cam follower on one of the two components is caused to move from a first position, in which the components are engaged, to a second position, in which the components are disengaged, wherein said disengagement involves physical, separation of two components which are required to interact in order for the inhaler device to be actuated;
   detection means for detecting the inhalation of a previously dispensed dose of medicament, whereby if the detection means detects the inhalation of the previously dispensed dose of medicament, the detection means releases the prevention means, allowing the inhaler device to dispense a further dose of medicament wherein said interlocking collar comprises stepped, interlocking surfaces with the cap, and one or more projections on the interlocking collar for engagement with one or more recesses on the inner surface of the housing.

2. The inhaler device as claimed in claim 1, wherein the actuation mechanism comprises a manually operable actuation means.

3. The inhaler device as claimed in claim 2, wherein the manually operable actuation means comprises a twist-action mechanism.

4. The inhaler device according to claim 2, wherein the prevention means acts on, and/or is associated with, the actuation mechanism.

5. The inhaler device as claimed in claim 4, wherein an initial operation of the actuation mechanism primes the inhaler device so as to dispense, or enable dispensing, of the plurality of doses of the medicament, but a further movement or operation of the actuation mechanism operates the prevention means, thereby preventing, at least temporarily, the dispensing of the further dose.

6. The inhaler device as claimed in claim 5, wherein the initial operation and further movement of the actuation mechanism represent different extents of movement in the same sense.

7. The inhaler device as claimed in claim 5, wherein the initial operation is movement in a first sense and the further movement is a reciprocal movement in the opposite sense or direction to the initial operation.

8. The inhaler device as claimed in claim 1, wherein the relative movement of the two components is brought about manually by the user of the inhaler device.

9. The inhaler device as claimed in claim 1, wherein the detection means comprises a pressure sensor.

10. The inhaler device as claimed in claim 9, wherein the pressure sensor is a micro electromechanical systems (MEMS) pressure sensor.

11. The inhaler device as claimed in claim 9, wherein the pressure sensor is responsive to a pressure reduction of 40-60 mbar.

12. The inhaler device as claimed in claim 9, wherein the pressure sensor is responsive to the duration of a change in pressure.

13. The inhaler device as claimed in claim 9, wherein the detection means is responsive only to a pressure reduction of a predetermined magnitude which persists for a predetermined length of time.

14. The inhaler device as claimed in claim 13, wherein the predetermined magnitude of the pressure reduction is 40-60 mbar and the predetermined length of time is at least 1 second.

15. The inhaler device as claimed in claim 1, wherein the detection means is positioned in, or in the vicinity of, an outlet or mouthpiece via which the dose of medicament is inhaled by the user.

16. The inhaler device as claimed in claim 1, which comprises one or more signal processing means.

17. The inhaler device as claimed in claim 16, wherein the signal processing means includes one or more of: a microprocessor, an amplifier for amplifying a signal output from the detection means, and signal filter means.

18. The inhaler device as claimed in claim 1, wherein the actuation mechanism is held in a disengaged state by a purely mechanical means that does not rely on a supply of electrical power.

19. The inhaler device as claimed in claim 18, wherein the mechanical means includes a latch mechanism that engages when components of the actuation mechanism are disengaged and then maintains the components in the disengaged state until the latch mechanism is released.

20. The inhaler device as claimed in claim 19, wherein a component of the actuation mechanism is formed with resilient detents that are adapted to hold that component in a position spaced apart from another component with which the first component is normally engaged, and which can be released to permit reengagement of the two components.

21. The inhaler device as claimed in claim 20, wherein release of the detents is brought about by electromechanical means.

22. The inhaler device as claimed in claim 1, wherein said inhaler device is a dry powder inhaler.

23. A method comprising administering a dose of a medicament to a user using an inhaler device as claimed in claim 1.

* * * * *